United States Patent
Watson

(10) Patent No.: US 9,999,835 B2
(45) Date of Patent: Jun. 19, 2018

(54) MOTION SICKNESS MONITORING AND APPLICATION OF SUPPLEMENTAL SOUND TO COUNTERACT SICKNESS

(71) Applicant: Sony Interactive Entertainment Inc., Tokyo, CA (US)

(72) Inventor: Brian Watson, Burlingame, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 269 days.

(21) Appl. No.: 14/615,115

(22) Filed: Feb. 5, 2015

(65) Prior Publication Data
US 2016/0228771 A1    Aug. 11, 2016

(51) Int. Cl.
*G06F 3/01* (2006.01)
*A63F 13/57* (2014.01)
(Continued)

(52) U.S. Cl.
CPC ............. *A63F 13/57* (2014.09); *A61B 3/112* (2013.01); *A61B 3/113* (2013.01); *A61B 5/1128* (2013.01); *A61B 5/4023* (2013.01); *A61B 5/4836* (2013.01); *A63F 13/212* (2014.09); *A63F 13/213* (2014.09); *A63F 13/26* (2014.09); *A63F 13/285* (2014.09); *A63F 13/424* (2014.09); *A63F 13/428* (2014.09); *A63F 13/54* (2014.09);
(Continued)

(58) Field of Classification Search
CPC ..... A61B 2503/12; A61B 3/112; A61B 3/113; A61B 5/1128; A61B 5/4023; A61B 5/4836; A61M 2021/0038; A63F 13/212; A63F 13/213; A63F 13/26; A63F 13/285; A63F 13/424; A63F 13/428; A63F 13/54; A63F 13/57; A63F 13/67; A63F 13/79; G06F 3/011; G06F 3/012; G06F 3/013; G06K 9/00671; G06T 19/006
See application file for complete search history.

(56) References Cited

U.S. PATENT DOCUMENTS 6,623,428 B2 *  9/2003  Miller ...................... H04N 1/00
                                                                  128/897
6,692,428 B1 *  2/2004  Kania ............... A61M 21/0094
                                                                  600/27
(Continued)

*Primary Examiner* — Justin Myhr
(74) *Attorney, Agent, or Firm* — Martine Penilla Group, LLP

(57) ABSTRACT

Methods, systems, and computer programs are presented for managing motion sickness of a user while the user is wearing a head-mounted device (HMD). One method includes an operation for monitoring the physical characteristics of the user while wearing the HMD that is presenting a virtual reality with multimedia content, where the physical characteristics including motions of the user. The multimedia content includes audio and video for presentation on a display of the HMD. Additionally, the method includes an operation for determining if the user is experiencing motion sickness based on the monitoring of the physical characteristics of the user while the virtual reality is being presented. When the user is experiencing motion sickness, supplemental sound is delivered to the user, where the supplemental sound is combined with sound from the multimedia content for delivery to the user, and the supplemental sound is defined to decrease the motion sickness experienced by the user.

19 Claims, 11 Drawing Sheets

(51) Int. Cl.
  *A63F 13/428* (2014.01)
  *A63F 13/26* (2014.01)
  *A63F 13/212* (2014.01)
  *A63F 13/285* (2014.01)
  *A63F 13/424* (2014.01)
  *A63F 13/213* (2014.01)
  *A63F 13/54* (2014.01)
  *A63F 13/67* (2014.01)
  *A63F 13/79* (2014.01)
  *A61B 3/11* (2006.01)
  *A61B 3/113* (2006.01)
  *A61B 5/11* (2006.01)
  *A61B 5/00* (2006.01)
  *G06K 9/00* (2006.01)
  *G06T 19/00* (2011.01)
  *A61M 21/00* (2006.01)

(52) U.S. Cl.
  CPC .............. *A63F 13/67* (2014.09); *A63F 13/79* (2014.09); *G06F 3/011* (2013.01); *G06F 3/012* (2013.01); *G06F 3/013* (2013.01); *G06K 9/00671* (2013.01); *G06T 19/006* (2013.01); *A61B 2503/12* (2013.01); *A61M 2021/0038* (2013.01)

(56) References Cited

U.S. PATENT DOCUMENTS

| | | | |
|---|---|---|---|
| 8,708,884 B1* | 4/2014 | Smyth | A61M 21/00 600/27 |
| 2009/0120429 A1* | 5/2009 | Fowler | H02S 20/00 126/704 |
| 2011/0009193 A1* | 1/2011 | Bond | A63F 13/212 463/36 |
| 2011/0081132 A1* | 4/2011 | Iwata | H04N 5/144 386/353 |
| 2012/0105483 A1* | 5/2012 | Fedorovskaya | G02B 27/017 345/660 |
| 2012/0134543 A1 | 5/2012 | Fedorovskaya et al. | |
| 2012/0259638 A1* | 10/2012 | Kalinli | G10L 15/25 704/270 |
| 2013/0038599 A1* | 2/2013 | Krakowski | H04H 60/04 345/419 |
| 2014/0176296 A1 | 6/2014 | Morgan | |
| 2014/0361976 A1 | 12/2014 | Osman et al. | |
| 2015/0325027 A1* | 11/2015 | Herman | G06T 13/00 345/633 |

* cited by examiner

MOTION SICKNESS MONITORING AND APPLICATION OF SUPPLEMENTAL SOUND TO COUNTERACT SICKNESS

BACKGROUND

1. Field of the Invention

The present embodiments relates to methods, systems, and programs for managing motion sickness while wearing a head-mounted device (HMD).

2. Description of the Related Art

Typically, an HMD is a portable device worn around the head of the user, such that a display situated a short distance from the eyes provides images for user interaction. In other cases, images are projected directly on the retina of the user. Sometimes HMDs provide virtual reality environments, where the user is able to see images created by a computing device. Some experiences are immersive, which means that motions of the player (e.g., turning the head) translate into corresponding changes in the view of the virtual reality, giving the illusion that the player is inside the virtual reality.

However, if the rate of change of the presentation of the virtual reality is not fast enough when the player is moving, the player my experience motion sickness, as the expected view does not correspond to what the user senses expected. Also, sometimes the action of the virtual reality may cause rapid changes in the view presented in the HMD, which could also result in motion sickness.

What is needed is an HMD that monitors for possible motion sickness of the user wearing the HMD, and takes action to reduce the motion sickness.

It is in this context that embodiments arise.

SUMMARY

Methods, devices, systems, and computer programs are presented for monitoring and managing motion sickness in a user wearing a head-mountain display (HMD). It should be appreciated that the present embodiments can be implemented in numerous ways, such as a method, an apparatus, a system, a device, or a computer program on a computer readable medium. Several embodiments are described below.

In one embodiment, a method is provided. The method includes an operation for monitoring physical characteristics of a user while the user is wearing a headmounted display (HMD) and the HMD is presenting a virtual reality with multimedia content, the multimedia content including video for presentation on a display of the HMD and audio, the physical characteristics including motions of the user. In addition, the method includes an operation for determining if the user is experiencing motion sickness based on the monitoring of the physical characteristics of the user while the virtual reality is being presented. When the user is experiencing motion sickness, supplemental sound is delivered to the user, where the supplemental sound is combined with sound from the multimedia content for delivery to the user, the supplemental sound being defined to decrease the motion sickness experienced by the user.

In another embodiment, a headmounted display (HMD) is presented. The HMD includes a display, speakers, a camera, and a processor. The display is for presenting a virtual reality with multimedia content, the speakers are for presenting sound of the multimedia content, and the camera is for tracking a gaze of a user when the user is wearing the HMD. The processor determines if the user is experiencing motion sickness based on the tracking of the gaze of the user, where when the user is experiencing motion sickness, the speakers deliver supplemental sound. The supplemental sound is defined to decrease the motion sickness experienced by the user, and the supplemental sound is combined with sound from the multimedia content for delivery via the speakers to the user.

In yet another embodiment, a non-transitory computer-readable storage medium storing a computer program is provided. The computer-readable storage medium includes program instructions for monitoring physical characteristics of a user wearing a headmounted display (HMD) while the user is accessing a virtual reality with multimedia content on the HMD, and program instructions for determining if the user is experiencing motion sickness based on the physical characteristics. Additionally, the storage medium includes program instructions for, when the user is experiencing motion sickness, delivering supplemental sound to the user, the supplemental sound defined to decrease the motion sickness experienced by the user. The supplemental sound is combined with sound from the multimedia content for delivery to the user.

Other aspects will become apparent from the following detailed description, taken in conjunction with the accompanying drawings.

BRIEF DESCRIPTION OF THE DRAWINGS

The embodiments may best be understood by reference to the following description taken in conjunction with the accompanying drawings.

DETAILED DESCRIPTION

The following embodiments describe methods, devices, systems, and computer programs for managing motion sickness for users wearing HMD's. When a user is interacting with a virtual reality (VR) space, e.g., a game or an application, sensors are used to determine if the user is experiencing motion sickness. Once it is determined that the user is experiencing, or is about to experience, motion sickness, the system can take measures to reduce motion sickness, such as by providing supplemental sound waves, which may be delivered via headphones or speakers in the HMD or via a separate ear piece.

It will be apparent, that the present embodiments may be practiced without some or all of these specific details. In other instances, well-known process operations have not been described in detail in order not to unnecessarily obscure the present embodiments.

Figure 1:
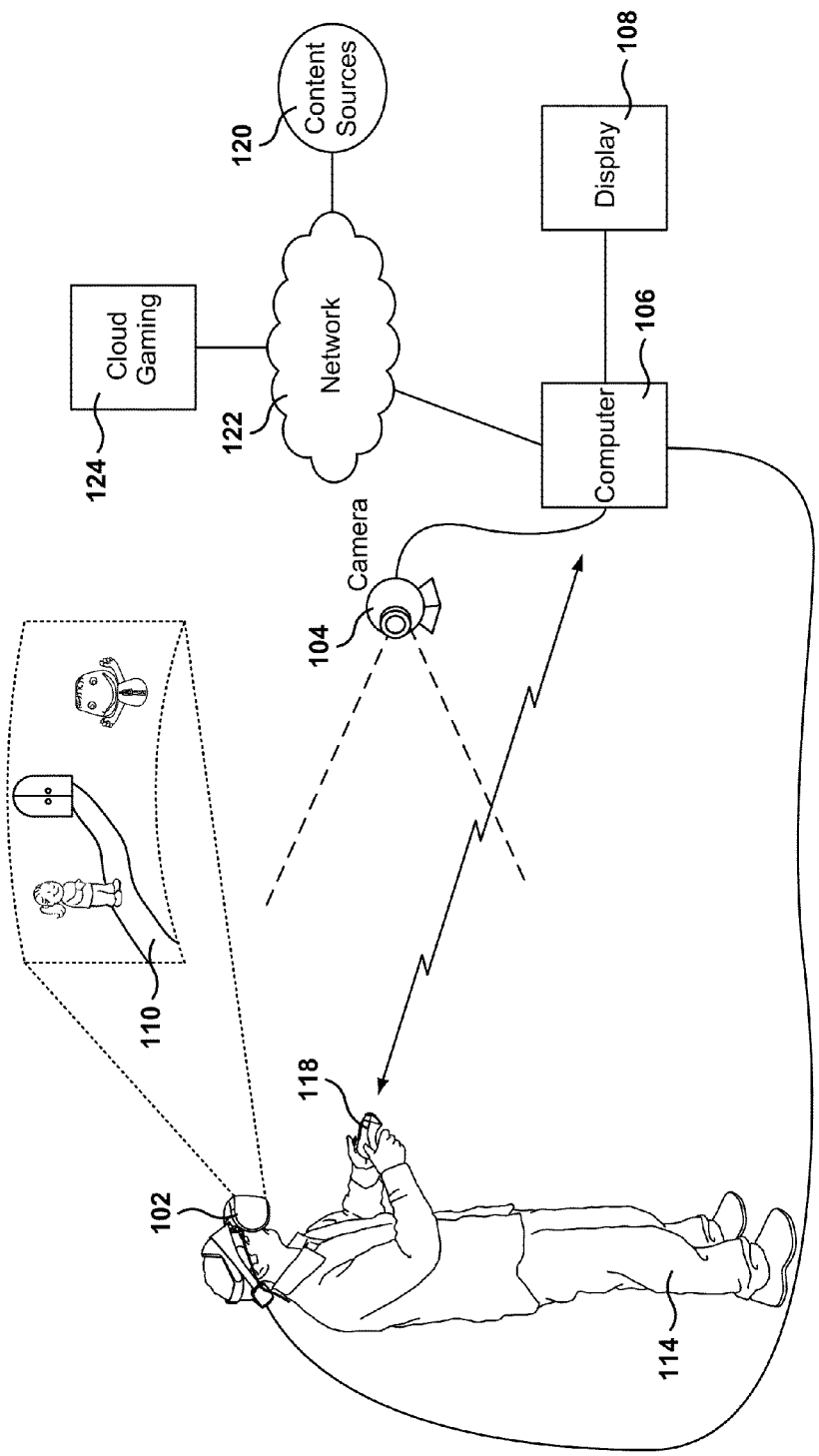
FIG. 1 illustrates a user interacting with a plurality of devices, including a Head Mounted Device (HMD), according to one embodiment.

FIG. 1 illustrates a system for interactive gameplay of a video game, in accordance with one embodiment. A user 114 is shown wearing a head-mounted display (HMD) 102. The HMD 102 is worn in a manner similar to glasses, goggles, or a helmet, and is configured to display a video game or other content to the user 114. The HMD 102 is configured to provide an immersive experience to the user by virtue of its provision of display mechanisms (e.g., optics and display screens) in close proximity to the user's eyes and the format of the content delivered to the HMD. In one example, the HMD 102 can provide display regions to each of the user's eyes which occupy large portions or even the entirety of the field of view 110 of the user. In another embodiment, images are projected directly into the retinas of the user.

In one embodiment, the HMD 102 can be connected to a computer 106. The connection to computer 106 can be wired or wireless. The computer 106 can be any general or special purpose computer, including but not limited to, a gaming console, personal computer, laptop, tablet computer, mobile device, cellular phone, tablet, thin client, set-top box, media streaming device, etc. In some embodiments, the HMD 102 can connect directly to the internet, which may allow for cloud gaming without the need for a separate local computer. In one embodiment, the computer 106 can be configured to execute a video game (and other digital content), and output the video and audio from the video game for rendering by the HMD 102. The computer 106 is also referred to herein as a client system 106, which in one example is a video game console. The processing of game operations may be done on the computing device 106, on the HMD 102, or in both computing device 106 and HMD 102.

The computer may, in some embodiments, be a local or remote computer, and the computer may run emulation software. In a cloud gaming embodiment, the computer is remote and may be represented by a plurality of computing services that may be virtualized in data centers, wherein game systems/logic can be virtualized and distributed to user over a network.

The user 114 may operate a controller 118 to provide input for the video game. In one example, a camera 104 can be configured to capture images of the interactive environment in which the user 114 is located. These captured images can be analyzed to determine the location and movements of the user 114, the HMD 102, and the controller 118. In one embodiment, the controller 118 includes a light (or lights) which can be tracked to determine its location and orientation. Additionally, the HMD 102 may include one or more lights which can be tracked as markers to determine the location and orientation of the HMD 102 in substantial real-time during game play. In one embodiment, the computing device 106 calculates a relative position between the HMD 102 and the game controller 116. The relative position is then used by the game to move a game object in synchronism with the HMD 102.

The camera 104 can include one or more microphones to capture sound from the interactive environment. Sound captured by a microphone array may be processed to identify the location of a sound source. Sound from an identified location can be selectively utilized or processed to the exclusion of other sounds not from the identified location. Furthermore, the camera 104 can be defined to include multiple image capture devices (e.g. stereoscopic pair of cameras), an infrared camera, a depth camera, and combinations thereof.

In some embodiments, computer 106 can execute games locally on the processing hardware of the computer 106. The games or content can be obtained in any form, such as physical media form (e.g., digital discs, tapes, cards, thumb drives, solid state chips or cards, etc.) or by way of download from the Internet, via network 122. In another embodiment, the computer 106 functions as a client in communication over a network with a cloud gaming provider 124. The cloud gaming provider 124 may maintain and execute the video game being played by the user 114. The computer 106 transmits inputs from the HMD 102, the controller 118 and the camera 104, to the cloud gaming provider, which processes the inputs to affect the game state of the executing video game. The output from the executing video game, such as video data, audio data, and haptic feedback data, is transmitted to the computer 106. The computer 106 may further process the data before transmission or may directly transmit the data to the relevant devices. For example, video and audio streams are provided to the HMD 102, whereas a vibration feedback command is provided to the controller 118.

In one embodiment, HMD 102, controller 118, and camera 104, may themselves be networked devices that connect to the network 122 to communicate with the cloud gaming provider 124. For example, the computer 106 may be a local network device, such as a router, that does not otherwise perform video game processing, but facilitates passage network traffic. The connections to the network by the HMD 102, controller 118, and camera 104 may be wired or wireless. In some embodiments, content executed on the HMD 102 or displayable on a display 108, can be obtained from any content source 120. Example content sources can include, for instance, internet websites that provide downloadable content and/or streaming content. In some examples, the content can include any type of multimedia content, such as movies, games, static/dynamic content, pictures, social media content, social media websites, etc.

A player 114 may be playing a game on the HMD 102, where such content is immersive 3D interactive content. The content on the HMD 102, while the player is playing, can be shared to a display 108. In one embodiment, the content shared to the display 108 can allow other users proximate to the player 114 or remote to watch along with the user's play. In still further embodiments, another player viewing the game play of player 114 on the display 108 may participate interactively with player 114. For example, a user viewing the game play on the display 108 may control characters in the game scene, provide feedback, provide social interaction, and/or provide comments (via text, via voice, via actions, via gestures, etc.) which enables users that are not wearing the HMD 102 to socially interact with player 114, the game play, or content being rendered in the HMD 102.

It is noted that the embodiments illustrated in FIG. 1 are exemplary. Other embodiments may utilize different devices, a different number of devices, have more or less interaction between the different devices, use other ways of communication (e.g. ultrasonic), facilitate a multiplayer game with two users wearing respective HMD's play the same game, etc. The embodiments illustrated in FIG. 1 should therefore not be interpreted to be exclusive or limiting, but rather exemplary or illustrative.

Figure 2:
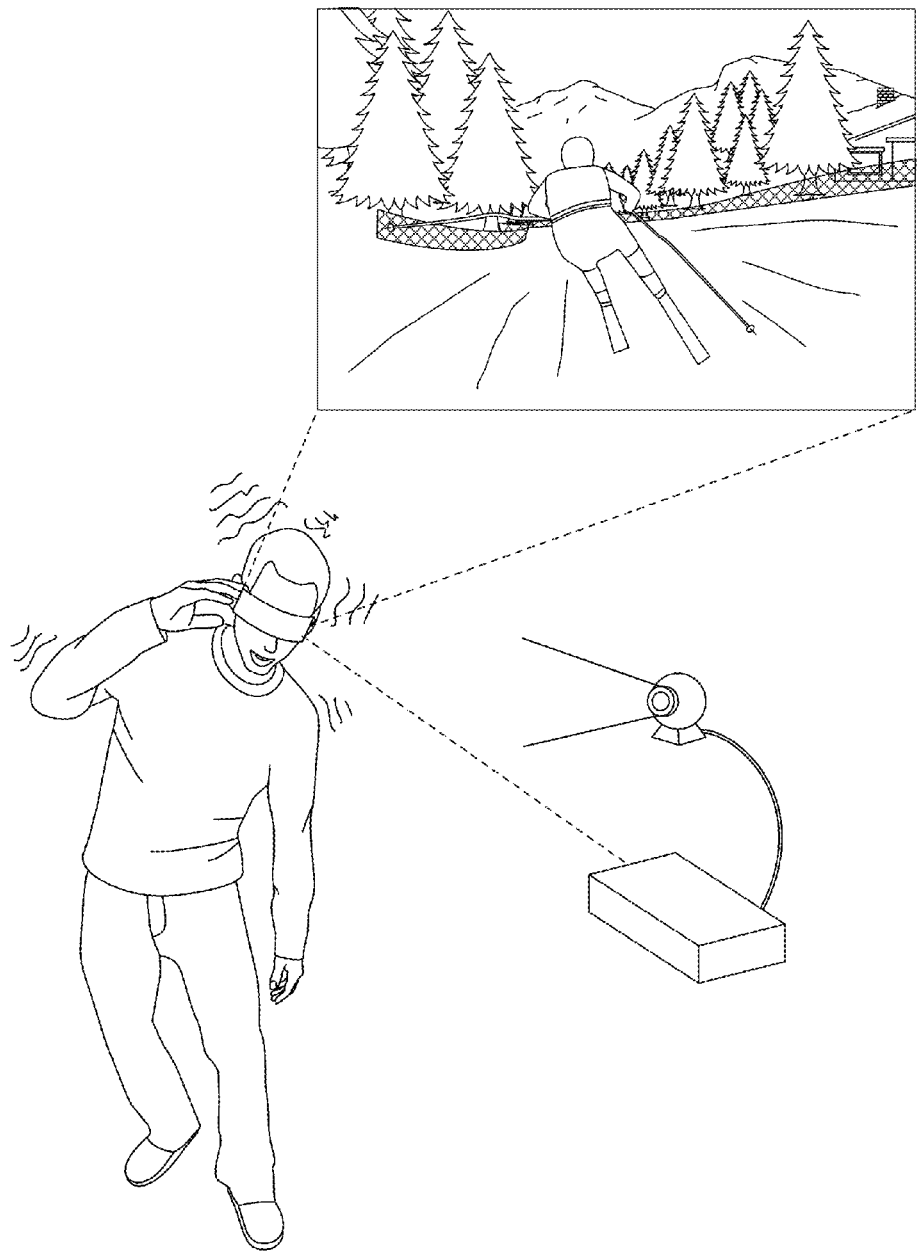
FIG. 2 depicts an HMD-wearing user experiencing motion sickness, according to one embodiment.

FIG. 2 depicts an HMD-wearing user experiencing motion sickness, according to one embodiment. The user wearing the HMD is immersed in a virtual reality game where an avatar is skiing downhill. In this particular example, the user is starting to feel motion sickness as the change in scenery is very fast, because the system has overloaded the senses of the user.

Motion sickness, also referred to as kinetosis or sometimes travel sickness, is a condition in which a disagreement exists between visually perceived movement and the vestibular system's sense of movement. Depending on the cause, motion sickness may also be referred to as seasickness, car sickness, simulation sickness or airsickness. Dizziness, fatigue, and nausea are the most common symptoms of motion sickness.

In one embodiment, the system monitors the user's physical characteristics, which may include one or more of body motion, or user pupil motion, or user gaze, or user head motion, or user balance. The system uses a plurality of sensors to monitor these physical characteristics. The sensors may include eye detection sensors in the HMD, motion sensors in the HMD (e.g., inertial sensors such as gyroscopes, accelerometers, and magnetometers), gaze detection sensors, facial sensors, other types of biometric sensors, or any combinations thereof. In addition, sensors outside the HMD may also be used to monitor the physical characteristics of the user, such as a camera coupled to a computing device that monitors the motions of the user. It is noted, that in some games the motion of the user is used as input to the game, such as tilting the body to one side or the other to change the direction of the skis in the downhill skiing game.

Motion sickness may be detected, for example, by tracking the movement of the eyes, or by detecting abnormal body movements (e.g., leaning to one side in a way not expected by the game activity taking place), or by tracking facial expressions of the user that may indicate motion sickness (e.g., a gagging motion, sticking out the tongue, etc.)

While wearing the HMD, the user may perceive sound from the multimedia content delivered by the HMD. The sound may be delivered via speakers in the HMD or via headphones on the ears. Sometimes, the HMD may include earpieces for placement in the user's ears, and some HMDs include connectors for plugging headsets to listen to the HMD-generated sound.

In embodiments presented herein, different motion-sickness fighting actions can be taken by the system when motion sickness is detected. The actions may include any of applying supplemental sound, reducing the intensity of the game, or vibrating the headset. In some embodiments, the actions to fight motion sickness may be applied even before motion sickness is detected, such as when the player is about to enter a very intense game section where motion sickness has a high probability of occurrence.

Figure 3:
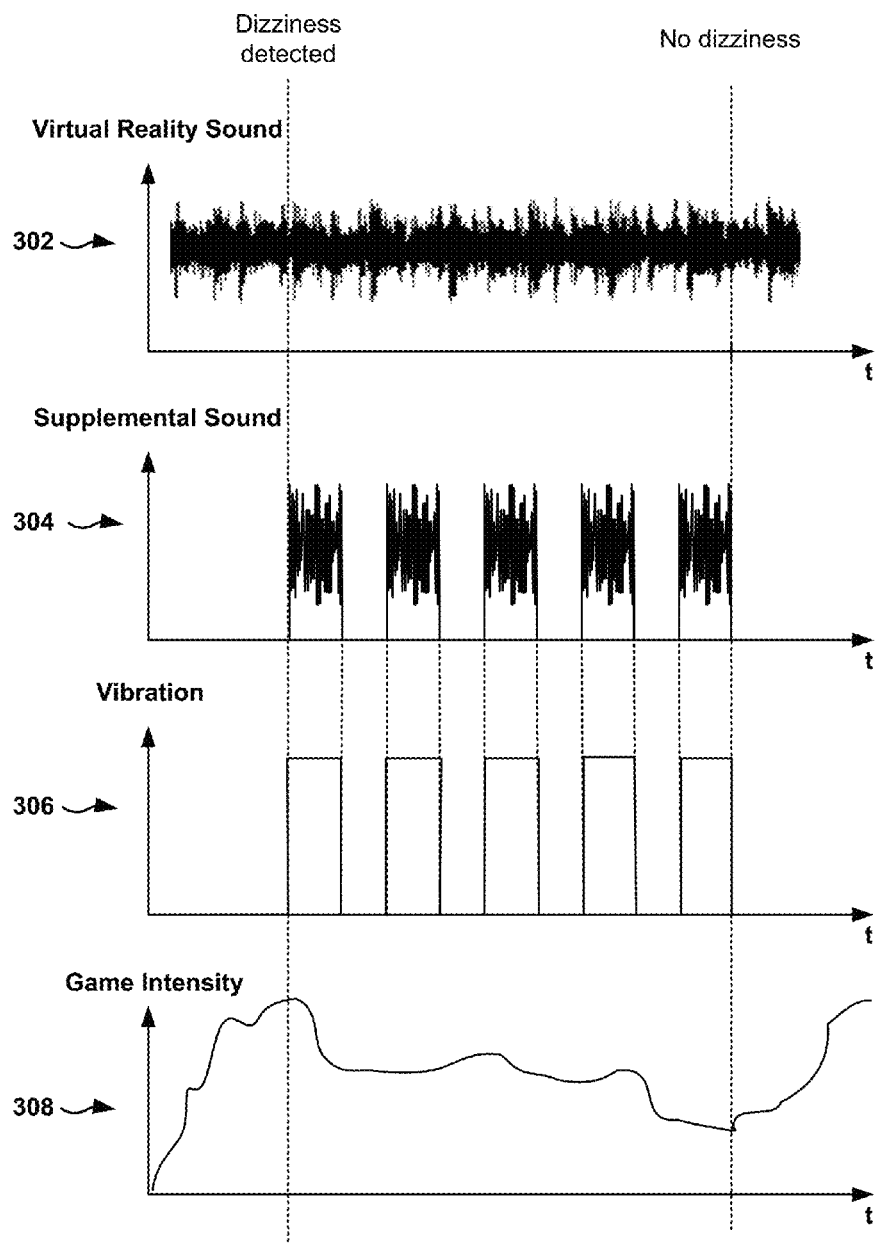
FIG. 3 illustrates the application of supplemental sound to control motion sickness, according to one embodiment.

FIG. 3 illustrates the application of supplemental sound to control motion sickness, according to one embodiment. Chart 302 illustrates virtual reality sound being delivered to the user wearing the HMD. As the user plays the game, the system monitors the user for any indicia that may indicate motion sickness.

In one embodiment, when motion sickness or any type of dizziness is detected, the HMD delivers a supplemental sound 304, which is combined with the game sound. The supplemental sound is a sound delivered to the user in order to decrease motion sickness symptoms in the user, and it has a therapeutic effect. In one embodiment, the supplemental sound is a series of pulses, but in another embodiment, the supplemental sound may be a constant acoustic signal delivered to the user. In one embodiment, the game sound may be altered when motion sickness is detected, such as by lowering the volume, applying a filter to the game sound to eliminate one or more areas of the spectrum for the audible signal, etc.

In another embodiment, the supplemental sound is delivered via bone conduction audio to stimulate the vestibular system. Bone conduction is the conduction of sound to the inner ear through the bones of the skull. The auditory system can be stimulated via sound energy that is sent through air to the ear drum (air conduction) or by placing a device or surface that can transmit vibrations to a bone, e.g., skull of the user, e.g., a device surface placed against, or contacting, the skull (e.g., the user's head, face, ear-surrounding surface, surface around a user's face, user's neck, or combinations of two or more thereof). In some embodiments, conducting sound via a user's bone or the skeletal structure is referred to as "bone conduction". Sound sent through air travels thorough all parts of the auditory system—the outer ear, middle ear, inner ear and central auditory pathways. In contrast, sound conducted through bone bypasses the outer and middle ear, directly setting up a traveling wave in the cochlea and stimulating the cochlea and central auditory pathways.

In one embodiment, bone conduction audio headsets can relay audio information to the user through a transducer that sits, or is placed, beside or proximate to the user's ear or in some other part of the skull or skeletal structure. This means that bone conduction audio is audible to the user receiving the bone conduction audio, but is nearly inaudible to others. In one embodiment, speakers capable of conducting this type of sound energy to provide bone conduction can be integrated as part of the HMD. In one embodiment, the vibration device can be incorporated into the strap of the HMD. For example, in addition to the speakers used to provide regular sound associated with the VR content, another speaker device or sound transducer can be coupled to or surround the headphones. In still other embodiments, a separate pad or device can be coupled to the user, e.g., around the user's ear. In still another embodiment, external speakers or vibration conducting devices may be connected to the HMD or interfaced with the HMD, or interfaced with the game console, for delivering bone conduction audio.

In this example bone conduction implementations, the sound, audio, vibration, energy, or combination of the two or more thereof, can be considered "supplemental sound," that is provided along with, or intermittently when needed, to assist users of the HMD from experiencing motion sickness at various phases of the interactions with the VR content.

The supplemental sound may be in-band or out-of-band of the sound frequencies delivered with the virtual reality. In one embodiment, the frequency or frequencies for the supplemental sound are preconfigured so the supplemental sound does not interfere with, or change, the sound fidelity of the virtual reality sound.

In some embodiments, the supplemental sound is in the audible spectrum, but in other embodiments, the supplemental sound may be ultrasonic, or a combination of both audible and ultrasonic sounds. The purpose of the supplemental sound is to introduce noise to the vestibular system, to stimulate the vestibular nerves of the inner ear, thereby, reducing motion sickness. It is believed that a gentle vibration noise will desensitize the brain of the user brain to the vestibular canal. This way, the user perception of motion sickness decreases.

In one embodiment, the supplemental sound is the only measure taken to fight motion sickness, but in other embodiments, a gentle vibration 306 may be also delivered to combat motion sickness. In another embodiment, the vibration is delivered to the user without the supplemental sound. The vibration may be in the form of pulses or may be a constant vibration delivered over a period of time. The vibration may include fast pulses, or slow pulses (e.g., the pulses are spaced over time such that the duration of the pulse is less than the period within pulses), or may be increased gradually in intensity over a period of time, or may be delivered as a sharp intense vibration with a short duration.

In one embodiment, the vibration is performed at a frequency that does not interfere with the fidelity of the virtual reality sound. The vibration may be applied next to the ear or to some other area of the head. It is believed that vibration applied in the skull next to the brain also helps reduce motion sickness. In one embodiment, the vibration pulses are synchronized with the supplemental sound pulses, but in other embodiments, they do not have to be synchronized, e.g., the vibration pulses and the supplemental sound pulses can be applied alternatively to combat motion sickness.

As discussed above, motion sickness may also be related to the intensity of the virtual reality and multimedia content delivered to the user, such as the intensity of a virtual reality game. Chart 308 illustrates an exemplary embodiment of the intensity delivered by a game. Initially, the game intensity keeps increasing, and eventually the game gets to a point where motion sickness is detected. In one embodiment, the intensity of the game is then decreased to help combat motion sickness.

In another embodiment, particular games or content can be flagged as possibly causing vertigo in particular scenes, times, or subject matter. For these types of rendering, the system can monitor the state of the user with higher fidelity. Then, if it is determined that motion sickness is occurring, the supplemental sound waves can be transmitted to one or both of the user's ears.

If it is known that the user is going to play in a high-intensity area of the game, where motion sickness has a higher than average probability to occur, the game may start applying measurements to avoid motion sickness, or to decrease potential motion sickness, such as by applying the supplemental sound even before motion sickness is detected. Therefore, the game may be proactive or reactive towards fighting motion sickness. The game may be proactive by applying measures before motion sickness is detected, or the game may be a reactive by applying measures after motion sickness is detected.

In some embodiments, the system tracks the profile of the user to identify user characteristics that may indicate the user propensity to get motion sickness. The sensibility may be based on past gaming experience, or other user characteristics, such as age, weight, height, medical history, etc. The game uses the user profile data to determine when to apply motion-sickness fighting methods. For example, if a first user is found not to be very susceptible to motion sickness, then the game will not apply any measures, but if a second user is found more susceptible, then the game may apply therapeutic measures to combat motion sickness, even when the second user is playing the game at the same game-intensity level as the first user.

More sensitive users will receive more therapeutic measures than less sensitive users. For example, older players may be more sensitive to motion sickness than young adults, or sedentary people may be more prompt to motion sickness than athletes. Also, more experienced players (in this game, and also more experienced in general with regards to virtual reality games) may be less prompt to motion sickness than newer players.

Figure 4:
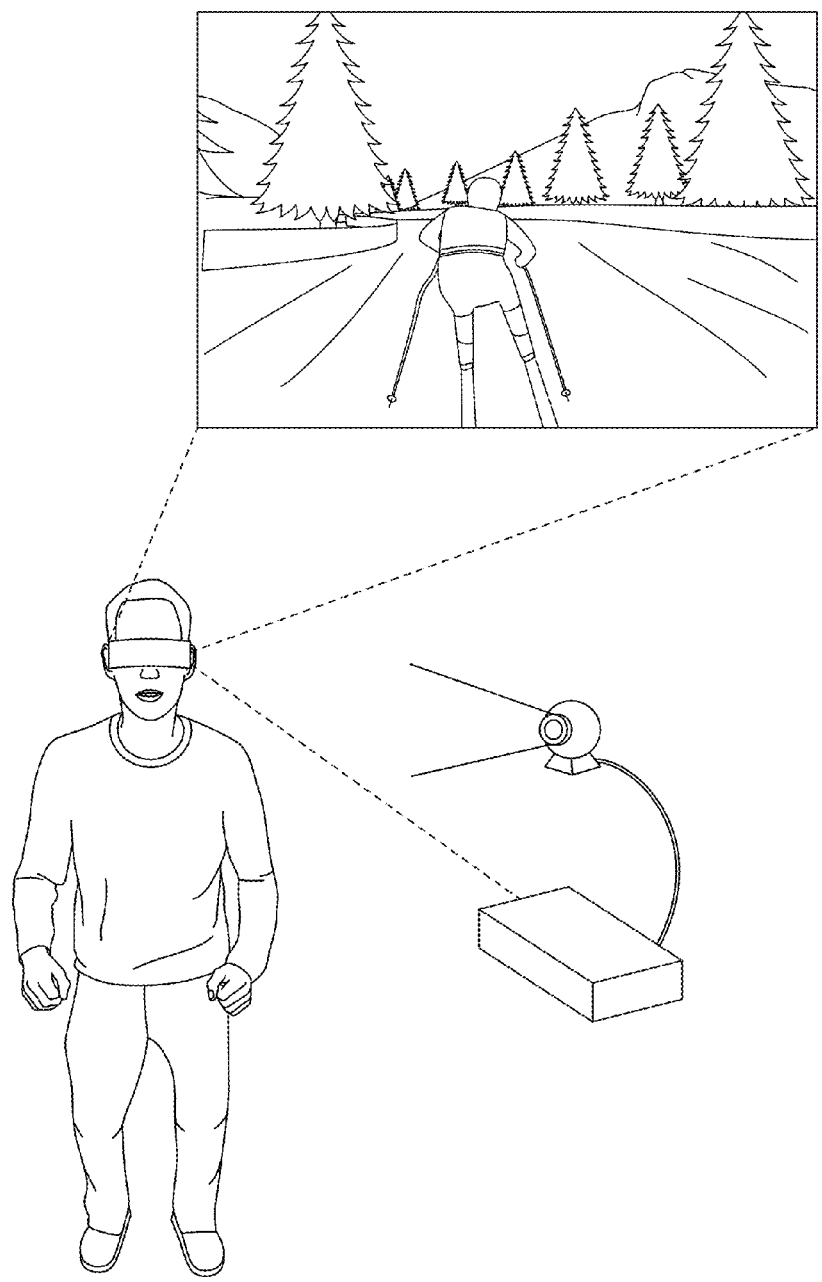
FIG. 4 depicts an HMD-wearing user playing a game, where the game intensity has been lowered to control motion sickness, according to one embodiment.

FIG. 4 depicts an HMD-wearing user playing a game, where the game intensity has been lowered to control motion sickness, according to one embodiment. The game intensity may be decreased in several ways, such as by reducing the speed of change on the display (e.g., slowing down the action and having the skier go slower and on a terrain that is less steep), reducing the number of elements on the display (e.g., less elements on the background such as trees, landscape), reducing the volume, reducing the spectrum for the game sound, reducing the number of colors on the display, or even freezing the display for a period of time. In one embodiment, the game may also add new elements to the display to reduce motion sickness, such as banners or geometric shapes that are simple and can help the user focus on what's happening in the game.

In one embodiment, the game system develops a historical map that identifies levels of motion sickness for different areas of the game, such as areas of the game within a virtual reality, or actions taken in the game (e.g., fighting an enemy). The historical map for motion sickness may be then applied to users playing the game, by identifying the areas where motion sickness is more probable, thereby, increasing measurements to detect motion sickness or applying proactive measures to avoid motion sickness.

In other embodiments, the supplemental sound can be by way of microwaves that are safe for the inner ear, or small sound pulses, or combinations thereof. Other forms of fighting motion sickness, include infrared stimulation, microwaves on the ear, vibration on the ear, small electric shocks, changing the weight distribution on the HMD, or other methods that affect the vestibular nerves.

In the exemplary embodiment of FIG. 4, the supplemental sound has been applied on the game intensity has been decreased by slowing the skier going downhill and taking out visual elements from the background (e.g., trees). The user is no longer experiencing motion sickness and is able to continue playing the game without discomfort.

Figure 5:
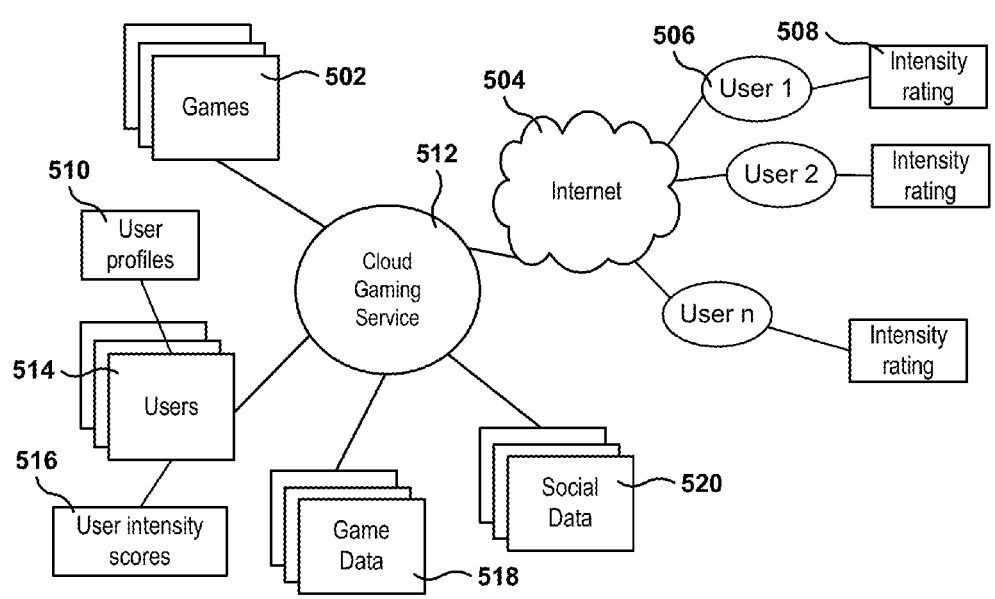
FIG. 5 illustrates an architecture for implementing embodiments presented herein.

FIG. 5 illustrates an architecture for implementing embodiments presented herein. In this illustration, the game content provided to the HMD is in a rich interactive 3-D space. The game content can be downloaded to a client system 506 or can be executed in one embodiment by a cloud gaming service 512. Cloud gaming service 112 can include a database of users 514, which are allowed to access particular games 502, share experiences with other friends, post comments, and manage their account information.

The cloud gaming service 512 can also store game data 518 for specific users, which may be usable during gameplay, future gameplay, sharing to a social media network, or for storing trophies, awards, status, ranking, etc. Social data 520 can also be managed by cloud gaming service 512. Cloud gaming service 512 may also include user profiles 510, where each user profile includes information about a user that may include one or more of user name, user demographic information, historical data, game data, intensity tags (also referred to herein as user intensity scores, or immersion scores, or immersion levels, or intensity ratings), motion sickness history, HMD configuration settings, social data, and other data.

The user intensity scores are also kept by the cloud gaming service 512. Additionally, the intensity scores 508 may also be kept or captured by the client systems. In one embodiment, cloud gaming service 512 cooperates with client devices 506 to share information regarding intensity levels, game data, user profile data, and social data.

The social data can be managed by a separate social media network, which can be interfaced with cloud gaming service 512 over the Internet 504. Over the Internet 504, any number of client systems 506 can be connected for access to the content and interaction with other users.

The three-dimensional interactive scene viewed in the HMD can include gameplay, such as the characters illustrated in the 3-D view. In one embodiment, a character or avatar is controlled by the user wearing the HMD.

Game logic may be executed in cloud gaming service 512, and client system 506, or in both. The game logic communicates with the different users playing the game in order to capture user data, including intensity ratings.

In one embodiment, the profile of the user includes data for the game being played. In one embodiment, the profile of the user includes at least one or more of the following values:
- user metadata
- user settings
- historical statistics
- historical motion sickness data
- sharing history
- multiplayer activities
- game scores
- intensity ratings
- intensity settings set by user for playing one or more games, including a default intensity setting
- levels played, and
- social screen The social screen is a presentation of the game being played with the HMD in a standard TV or PC display allowing users without the HMD to follow the game action and even participate in the game. The social screen may be presented to users near the HMD-wearing user or to remote users connected over a network.

It is noted that the embodiments illustrated in FIG. 5 are exemplary. Other embodiments may utilize different data organization, or organize the same data in a different way, or combine the data into a single database, etc. The embodiments illustrated in FIG. 5 should therefore not be interpreted to be exclusive or limiting, but rather exemplary or illustrative.

Figure 6A:
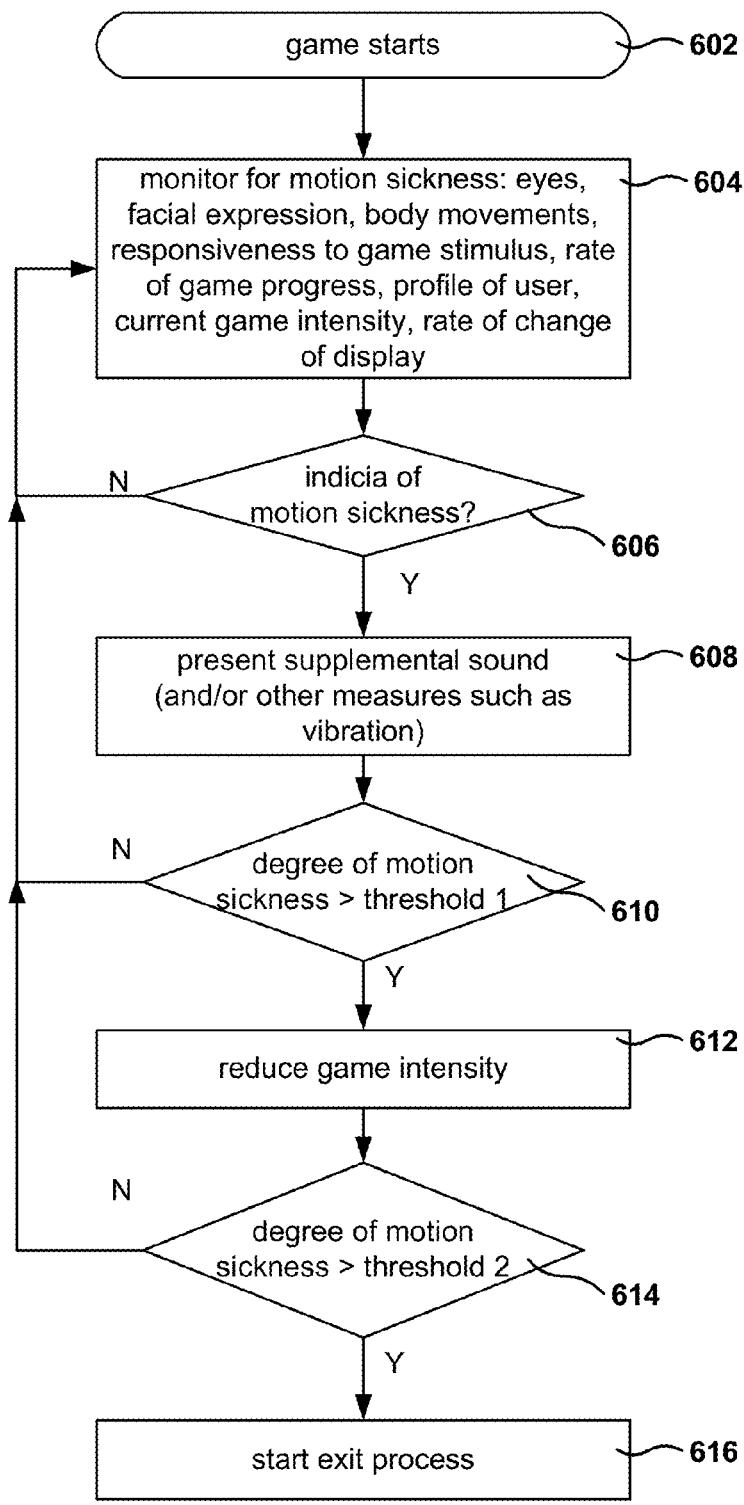
FIG. 6A is a flowchart for methods to control motion sickness, according to one embodiment.

FIG. 6A is a flowchart of a method for controlling motion sickness, according to one embodiment. While the various operations in this flowchart are presented and described sequentially, one of ordinary skill will appreciate that some or all of the operations may be executed in a different order, be combined or omitted, or be executed in parallel.

In operation 602, the virtual reality game starts, the virtual reality delivering multimedia content via the HMD. From operation 602, the method flows to operation 604 where the system (e.g., the HMD and the external computing device coupled to a camera, or a combination thereof), monitors the user for any signs of motion sickness (such as tracking of the eyes, facial expressions, body movements, responsiveness to game stimulus, rate of game progress, user profile, current game intensity, or rate of change of display).

From operation 604, the method flows to operation 606 where a check is made to determine if there are any indicia of motion sickness. If there are signs of motion sickness, the method flows to operation 608, and if there are no signs of motion sickness, the method flows back to operation 604 to continue monitoring the user for motion sickness.

In operation 608, supplemental sound is presented to the user, and optionally, other measures such as by vibrating the HMD. In one embodiment, the particular anatomy of the user is considered to adjust the way supplemental sound is delivered to the user. One example of a sound localization function is a Head-Related Transfer Function (HRTF), which is a response that characterizes how an ear receives a sound from a point in space. A pair of HRTFs for the ears may be utilized to synthesize a binaural sound that seems to come from a particular point in space. The HRTF can also be described as the modifications to a sound from a direction in free air to the sound arriving at the eardrum. These modifications include the shape of the listener's outer ear, the shape of the listener's head and body, the acoustical characteristics of the space in which the sound is played, and so on. All these characteristics influence how a listener can accurately tell what direction a sound is coming from. Due to the physical differences of each person, each person has a different HRTF. In some embodiments, HRTF is used to customize sound delivered to the user, but any other form of sound localization that accounts for the physical characteristics of a listener can be utilized with the presented embodiments.

From operation 608, the method flows to operation 610 where the degree of the amount of motion sickness experienced by the user is checked against a first threshold. If the degree of motion sickness is greater than the first threshold, the method flows to operation 612 where the game intensity is reduced to combat motion sickness. If the degree of motion sickness is not greater than the first threshold, the method flows back to operation 604 to continue monitoring the user.

From operation 612, the method flows to operation 614 where a check is made to determine if the degree of motion sickness is greater than a second threshold. If the degree of motion sickness is greater than the second threshold, the method flows to operation 616 where an exit procedure is initiated to allow the user to take off the HMD.

Figure 6B:
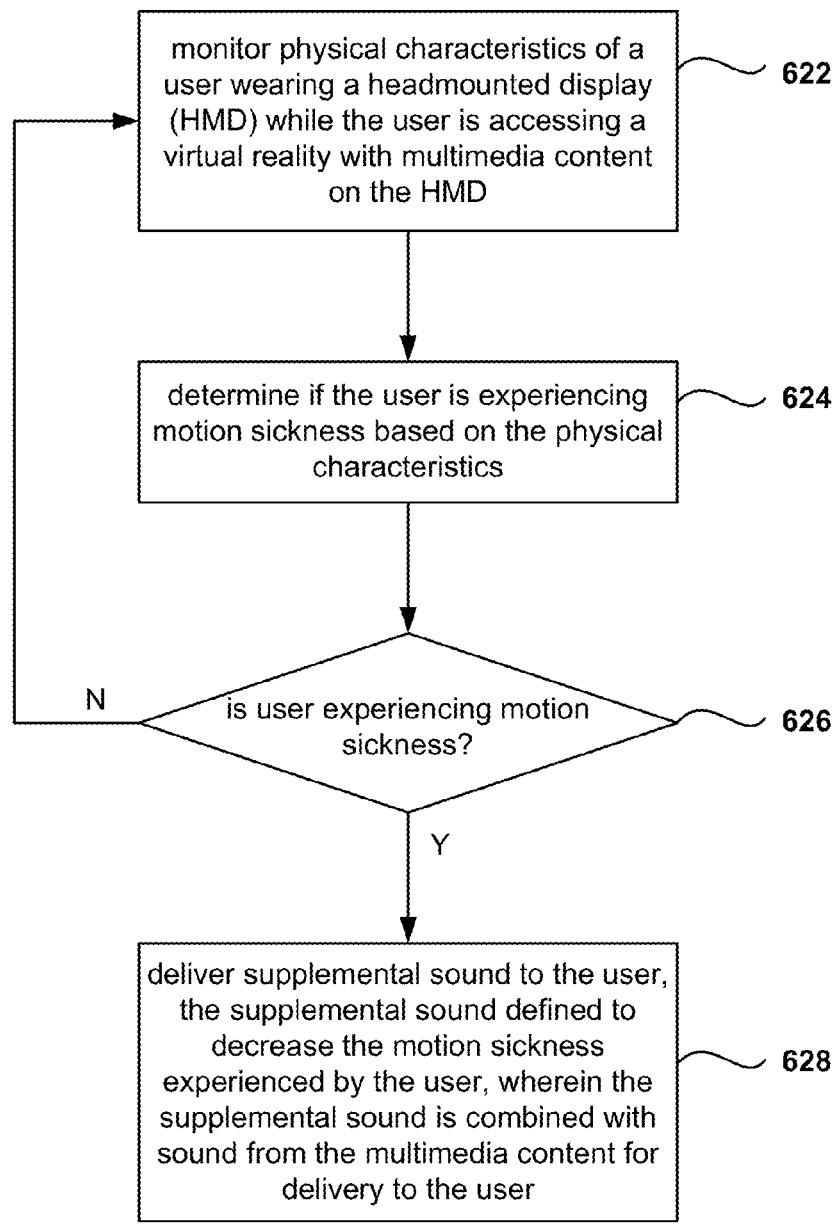
FIG. 6B is a flowchart for delivering supplemental sound to control motion sickness, according to one embodiment.

FIG. 6B is a flowchart for delivering supplemental sound to control motion sickness, according to one embodiment. While the various operations in this flowchart are presented and described sequentially, one of ordinary skill will appreciate that some or all of the operations may be executed in a different order, be combined or omitted, or be executed in parallel.

Operation 622 is for monitoring physical characteristics of a user while the user is wearing a headmounted display (HMD) and the HMD is presenting a virtual reality with multimedia content. The multimedia content includes video for presentation on a display of the HMD and audio, and the physical characteristics include motions of the user.

From operation 622, the method flows to operation 624 for determining if the user is experiencing motion sickness based on the monitoring of the physical characteristics of the user while the virtual reality is being presented. From operation 624, the method flows to operation 626 where a check is made to determine if the user is experiencing motion sickness.

If the user is not experiencing motion sickness, the method flows back to operation 622, but if the user is experiencing motion sickness, the method flows to operation 628, where supplemental sound is delivered to the user. The supplemental sound is combined with sound from the multimedia content for delivery to the user, and the supplemental sound is defined to decrease the motion sickness experienced by the user.

Figure 7A:
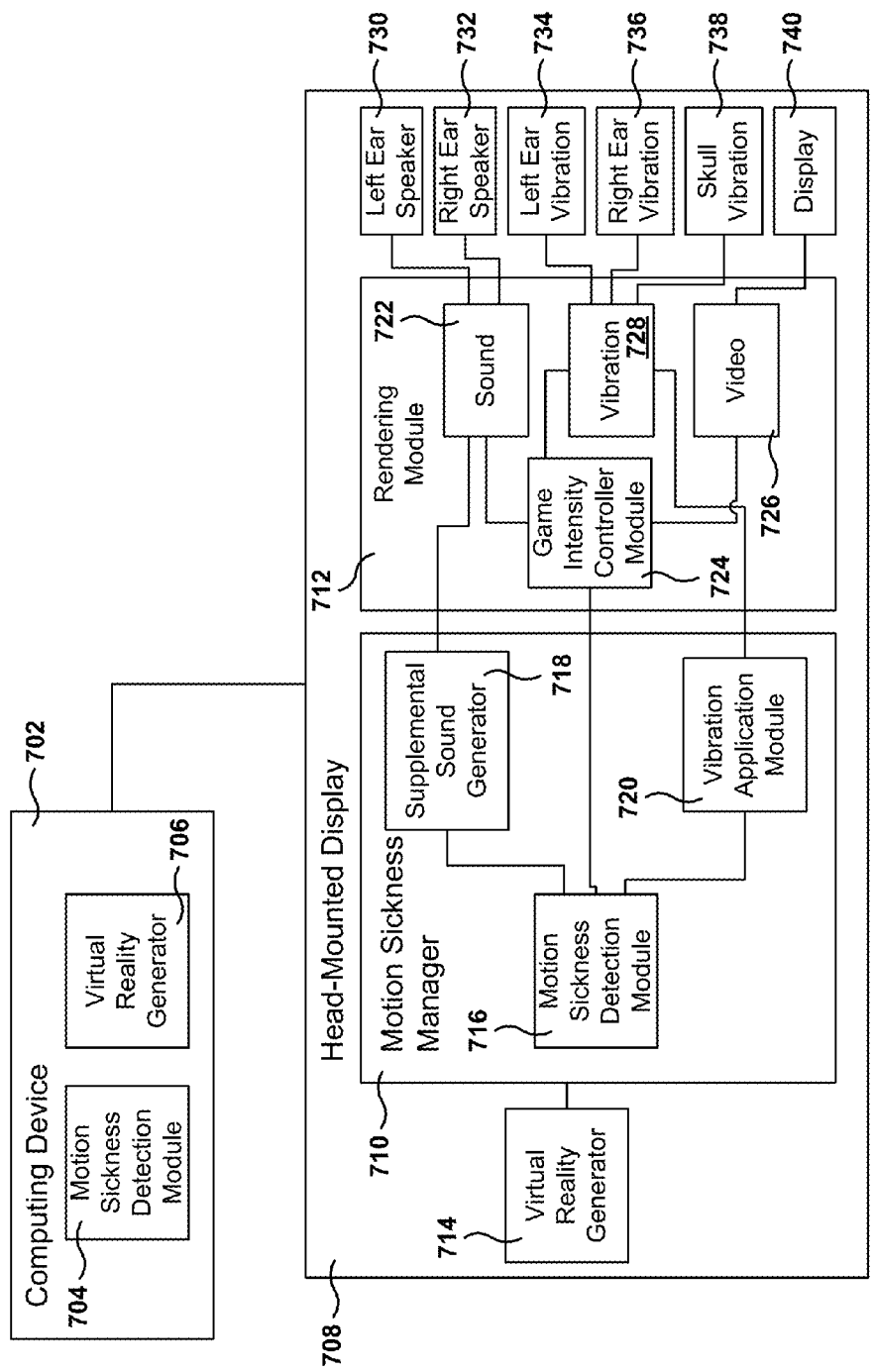
FIG. 7A illustrates the architecture of an HMD for delivering supplemental sound, according to one embodiment.

FIG. 7A illustrates the architecture of an HMD 708 for delivering supplemental sound, according to one embodiment. In one embodiment, HMD 708 cooperates with a computing device 702 to deliver virtual reality and multimedia content in the HMD. The system monitors the user to detect possible motion sickness and generate actions to combat motion sickness.

In one embodiment, the computing device 702 includes motion sickness detection module 704 and virtual reality generator 706. The motion sickness detection module 704 monitors the user for possible motion sickness. For example, in one embodiment, motion sickness detection module 704 monitors the motions of the user by analyzing images taken by a camera aimed at the user. In addition, motion sickness detection module 704 may utilize information transmitted from the HMD regarding the user, such as sensor data from inertial sensors in the HMD, or a user gaze data from a module that tracks the gaze of the user within the HMD.

The virtual reality generator 706 creates data for presenting a virtual reality world in the HMD. In one embodiment, the HMD displays the data received from the virtual reality generator 706, and in another embodiment, the virtual reality generator 706 cooperates with rendering module 712 in the HMD for presenting the virtual reality.

In one embodiment, HMD 708 includes virtual reality generator 714, motion sickness manager 710, rendering module 712, speakers, vibration modules, and display 740. Virtual reality generator 714 receives data from the computer device 702 and processes virtual reality data for presenting the virtual reality on the devices within the HMD (e.g., display 740, left-ear speaker 730, right-ear speaker 732, or even a sound jack (not shown) for delivering audio through one or more external speakers).

Motion sickness manager 710 includes a motion sickness detection module 716 that tracks the physical characteristics (e.g., motion, gaze) of the user, and determines if the user is experiencing motion sickness. In one embodiment, motion sickness is predicted based on the game intensity and the user profile, and therapeutic measures for fighting motion sickness may be deployed even before the user starts feeling motion sickness.

Motion sickness manager 710 further includes a supplemental sound generator 718, which generates supplemental sound for delivery to the user, as described above with reference to FIG. 3, and a vibration application module 710 for delivering vibrations to the user in order to combat motion sickness. The vibration delivered may be mechanical (e.g., generated by a device with moving parts that generate vibration) or might be sound vibration, which is delivered via one or more speakers.

The rendering module 712 includes a game intensity controller module 724, a sound module 722, a vibration module 728, and a video module 726. The game intensity controller module 724 is invoked when the motion sickness detection module 716 determines that the HMD must lower the game intensity to combat motion sickness. The game intensity controller module 724 may modify the delivery of multimedia content in order to lower the intensity, and/or communicate to the virtual reality generator 706 in computing device 702 so the virtual reality generator 706 lower the intensity for the virtual reality (e.g., game).

Further, the game intensity controller module 724 may control the sound, the vibration, or the video delivered to the user. The sound module 722 generates sound for the left-ear speaker 730 and the right-ear speaker 732. The vibration module 728 may generate vibrations to stimulate the vestibular system of the user, by generating vibration in the left ear 734, or vibration in the right ear 736, or by generating other type of vibration, such as by delivering a haptic vibration to the skull of the user 738 (e.g., on top of the head) through the skin, or to the face, or to any other part of the body in contact with the HMD.

The devices that generate the vibration may include a transducer, a piezoelectric transducer, a tuning fork, a motor, a fan, or any other device that may generate vibration. The vibration may be constant over a period of time, or may be in the form of intermittent pulses. In one embodiment, the vibration may change frequency over time to further stimulate the vestibular system.

It is noted that some of the connections between modules in FIG. 7A have been omitted to not obscure the elements presented, but in other embodiments, any type of communication between any of the modules in FIG. 7A is possible. In addition, the embodiments illustrated in FIG. 7A are exemplary. Other embodiments may utilize different modules, combine the functionality of two or more modules into a single module, distribute the functionality differently between operations performed at the computing device 702 and operations performed at an HMD 708, etc. The embodiments illustrated in FIG. 7A should therefore not be interpreted to be exclusive or limiting, but rather exemplary or illustrative.

Figure 7B:
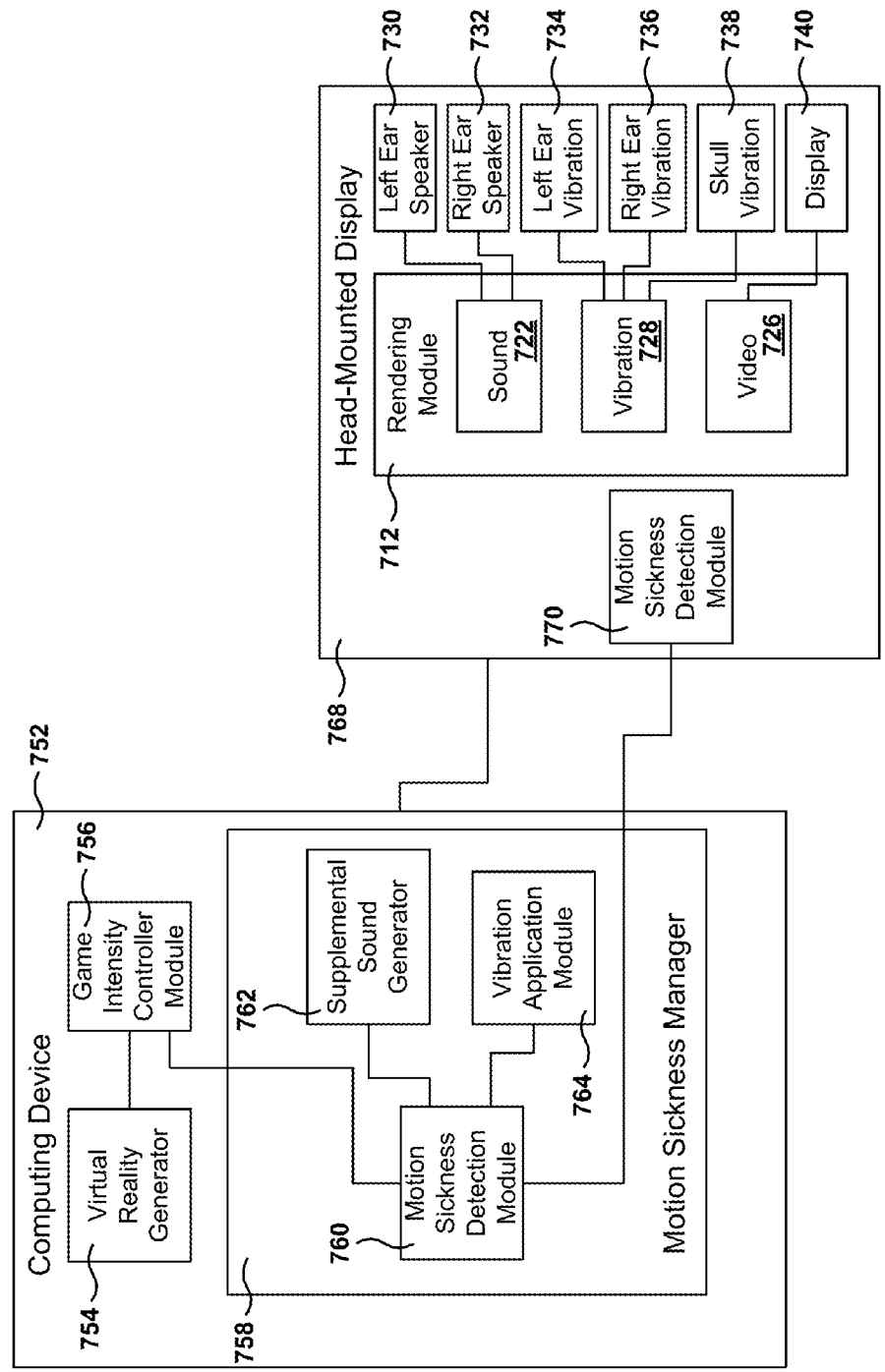
FIG. 7B illustrates an architecture of a system for delivering supplemental sound, according to one embodiment.

FIG. 7B illustrates an architecture of a system for delivering supplemental sound, according to one embodiment. FIG. 7B illustrates another embodiment, where motion sickness is controlled primarily by the computing device 752 in communication with HMD 768.

Computing device 752 includes virtual reality generator 754 and game intensity controller module 756. The virtual reality generator 754 generates the multimedia stream for presenting the virtual reality in the HMD 768. The game intensity controller module 756 is operable to adjust the intensity of the multimedia content delivered in the HMD. In one embodiment, the game intensity (e.g., virtual reality intensity) is controlled in order to avoid discomfort in the user wearing the HMD.

The computer device 752 further includes a motion sickness manager 758, which includes a motion sickness detection module 760, a supplemental sound generator 762, and a vibration application module 764. The modules within the motion sickness manager 758 communicate with respective modules in the HMD in order to monitor the user for motion sickness, deliver supplemental sound to the user, or deliver vibrations in the HMD to combat motion sickness.

HMD 768 includes motion sickness detection module 770, which cooperates with the motion sickness detection module 760 in the computer device to take actions to avoid or diminish motion sickness while wearing the HMD.

The HMD 768 further includes a rendering module 712, left-ear speaker 730, right-ear speaker 732, left-ear vibration module 734, right-ear vibration module 736, skull vibration module 738, and display 740. The rendering module 712 includes sound 722, vibration 728, and video 726 modules, which communicate with the respective peripherals in order to deliver sound, vibration, or video.

It is noted that some of the connections between modules in FIG. 7B have been omitted to not obscure the elements presented, but in other embodiments, any type of communication between any of the modules in FIG. 7B is possible. In addition, the embodiments illustrated in FIG. 7BA are exemplary. Other embodiments may utilize different modules, combine the functionality of two or more modules into a single module, etc. The embodiments illustrated in FIG.

7B should therefore not be interpreted to be exclusive or limiting, but rather exemplary or illustrative.

Figure 8:
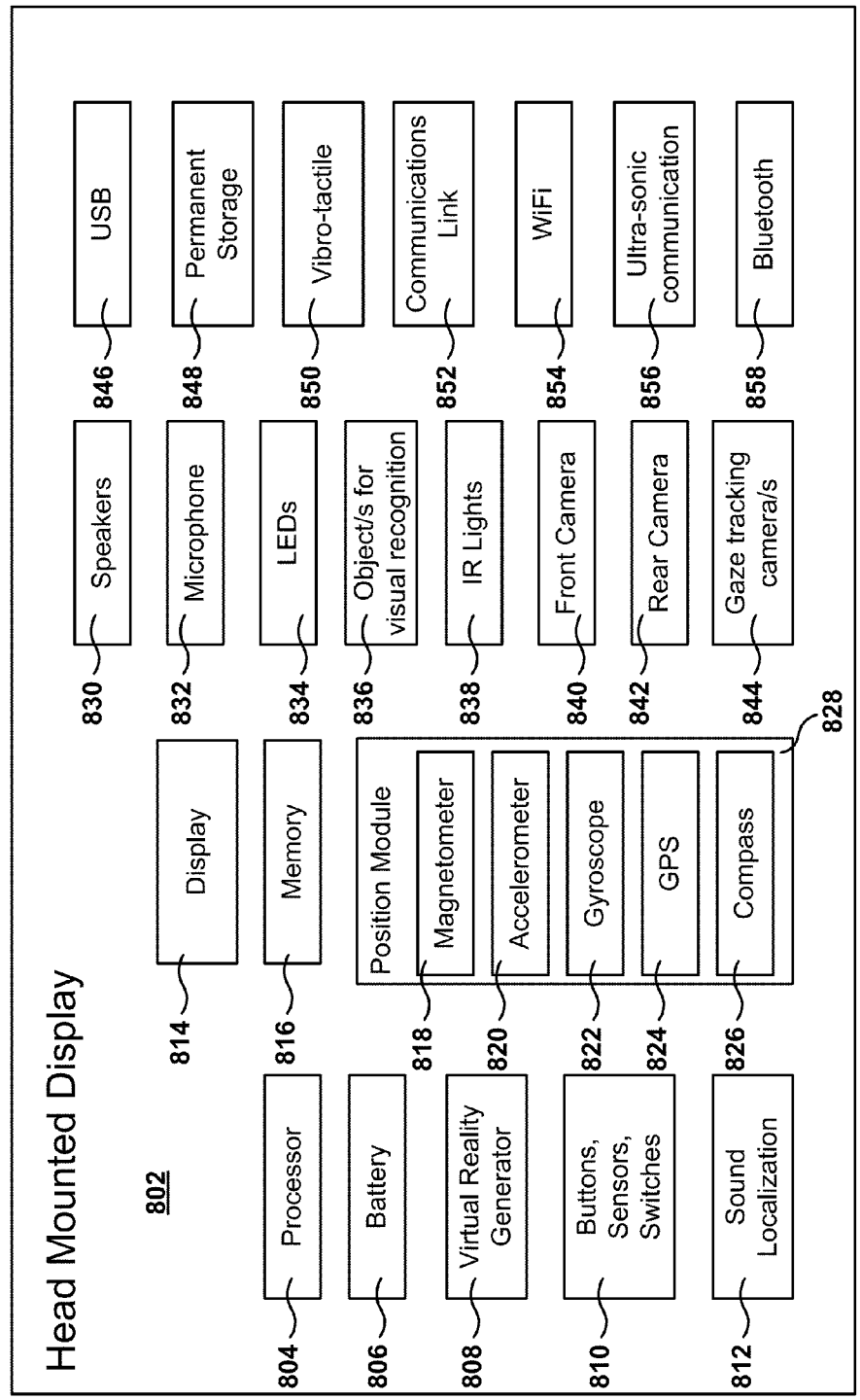
FIG. 8 illustrates the architecture of a device that may be used to implement some embodiments.

FIG. 8 illustrates the architecture of a device that may be used to implement embodiments. The head mounted display is a computing device and includes modules usually found on a computing device, such as a processor 804, memory 816 (RAM, ROM, etc.), one or more batteries 806 or other power sources, and permanent storage 848 (such as a hard disk).

The communication modules allow the HMD to exchange information with other portable devices, other computers, other HMD's, servers, etc. The communication modules include a Universal Serial Bus (USB) connector 846, a communications link 852 (such as Ethernet), ultrasonic communication 856, Bluetooth 858, and WiFi 854.

The user interface includes modules for input and output. The input modules include input buttons, sensors and switches 810, microphone 832, touch sensitive screen (not shown, that may be used to configure or initialize the HMD), front camera 840, rear camera 842, gaze tracking cameras 844. Other input/output devices, such as a keyboard or a mouse, can also be connected to the portable device via communications link, such as USB or Bluetooth.

The output modules include the display 814 for rendering images in front of the user's eyes. Some embodiments may include one display, two displays (one for each eye), micro projectors, or other display technologies. Other output modules include Light-Emitting Diodes (LED) 834 (which may also be used for visual tracking of the HMD), vibro-tactile feedback 850, speakers 830, and sound localization module 812, which performs sound localization for sounds to be delivered to speakers or headphones, providing a 3D sound simulation for objects rendered or displayed in the HMD to provide real-time 3D effect sounds. In one embodiment, speakers 830 may be sonic or ultrasonic. Other output devices, such as headphones, can also connect to the HMD via the communication modules. In one embodiment, vibro-tactile feedback 850 may be configured to deliver vibration to the skull of the user to combat motion sickness, or to deliver vibration to the vestibular system or the user, or to any other part of the head that may help combat motion sickness.

The elements that may be included to facilitate motion tracking include LEDs 834, one or more objects for visual recognition 836, and infrared lights 838.

Information from different devices can be used by the Position Module 828 to calculate the position of the HMD. These modules include a magnetometer 818, an accelerometer 820, a gyroscope 822, a Global Positioning System (GPS) module 824, and a compass 826. Additionally, the Position Module can analyze sound or image data captured with the cameras and the microphone to calculate the position. Further yet, the Position Module can perform tests to determine the position of the portable device or the position of other devices in the vicinity, such as WiFi ping test or ultrasound tests.

A Virtual Reality Generator 808 creates the virtual or augmented reality, as previously described, using the position calculated by the Position Module. The virtual reality generator 808 may cooperate with other computing devices (e.g., game console, Internet server, etc.) to generate images for the display module 814. The remote devices may send screen updates or instructions for creating game objects on the screen.

The HMD 802 may be used for playing games, as discussed above, or for any other immersive experience. In one embodiment, the HMD is used for virtual inspection of a real world location, such as a hotel. This way, a user considering whether to go to a certain hotel may take a virtual tour with the HMD to check the hotel facilities and accommodations. In one embodiment, if the user likes the hotel, the user may also get reservations for the hotel during the virtual tour by accessing a menu that provides prices, choices, and available dates.

In another embodiment, the HMD may be used for shopping, such as by traveling with the HMD through a real store or a virtual store. As the user moves around the store, the user is able to check different items (e.g., articles for sale). If the user wants to purchase one or more items, a menu is provided for checking out the articles desired (e.g., virtual checkout).

In another embodiment, the virtual tour may be used for virtual tourism, allowing the HMD-wearing user to travel different locations around the world (e.g., the wall of China, the Golden Gate Bridge, the Eiffel Tower, etc.). An option may be provided to allow the user to do travel reservations to visit the desired location.

In one embodiment, the HMD is used for education. Students may access virtual lessons immersed in a virtual reality, or students may access class materials, in a classroom setting, using the HMD. For example, our students can travel through a virtual museum with a teacher, which provides description about the different pieces of art. In one embodiment, the view of the HMD is set by the teacher and the student's travel the virtual world sharing the same images as the teacher. This way, students may not wonder and visit other areas of the museum while the teacher is given a lecture.

In one embodiment, the rendering engine for the virtual reality generator utilizes forward prediction for the motions of the user, predicting which parts of the virtual world will the user visit. For example, if the user starts turning the head to the right, the rendering engine will start generating data to the right of the current view assuming that the user will continue turning to the right. Additionally, the rendering engine may provide higher resolution to the images on the right that the images on the left, because the user is turning her attention towards the right.

In one embodiment, an Application Programming Interface (API) is provided for developers to access the functionality of the HMD. The API may be provided for programs to be executed on the HMD, as well as for remote calls to access functionality within the HMD. In addition, the API may provide interfaces for accessing another device that is associated with the HMD, such as a game console in communication with the HMD, or any other devices interfacing with the HMD (e.g., a camera connected to the game console that tracks the movements of the user wearing the HMD). In one embodiment, a Software Development Kit (SDK) is provided to assist developers in creating applications that exploit the functionality of the API.

It should be appreciated that the embodiment illustrated in FIG. 8 is an exemplary implementation of a portable device. Other embodiments may utilize different modules, a subset of the modules, or assign related tasks to different modules. Additionally, the elements of the HMD may have different sizes, with some HMDs having miniaturized components to reduce a size of the HMD. In one embodiment, the HMD may look like a pair of glasses, where the virtual or augmented worlds are presented on the glass of the glasses or projected onto the retina of the user wearing the HMD. The embodiment illustrated in FIG. 8 should therefore not be interpreted to be exclusive or limiting, but rather exemplary or illustrative.

Figure 9:
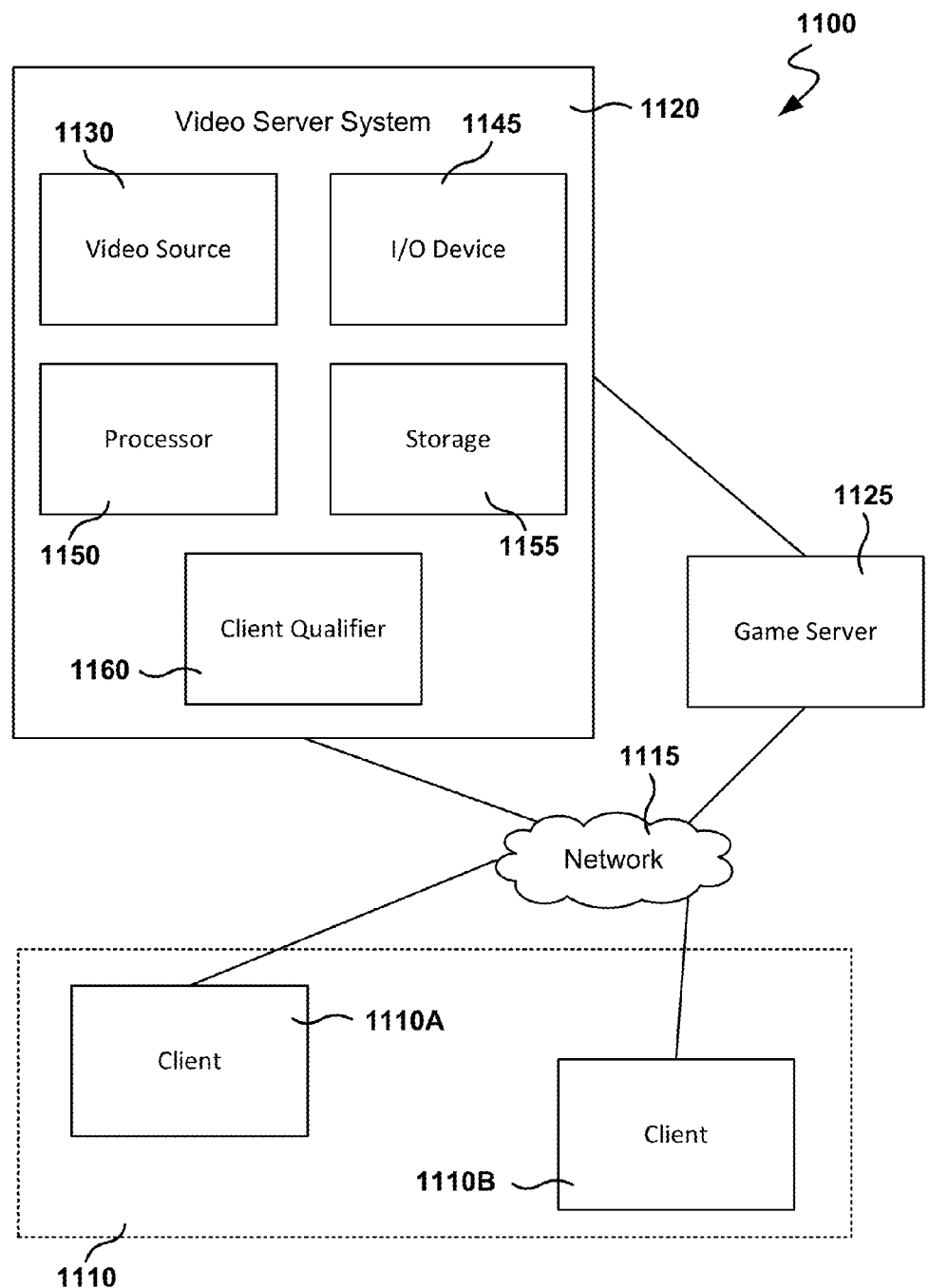
FIG. 9 is a block diagram of a game system, according to various embodiments.

FIG. 9 is a block diagram of a Game System 1100, according to various embodiments. Game System 1100 is configured to provide a video stream to one or more Clients 1110 via a Network 1115. Game System 1100 typically includes a Video Server System 1120 and an optional game server 1125. Video Server System 1120 is configured to provide the video stream to the one or more Clients 1110 with a minimal quality of service. For example, Video Server System 1120 may receive a game command that changes the state of or a point of view within a video game, and provide Clients 1110 with an updated video stream reflecting this change in state with minimal lag time. The Video Server System 1120 may be configured to provide the video stream in a wide variety of alternative video formats.

Clients 1110, referred to herein individually as 1110A, 1110B, etc., may include head mounted displays, terminals, personal computers, game consoles, tablet computers, telephones, set top boxes, kiosks, wireless devices, digital pads, stand-alone devices, handheld game playing devices, and/or the like. Typically, Clients 1110 are configured to receive encoded video streams, decode the video streams, and present the resulting video to a user, e.g., a player of a game. The processes of receiving encoded video streams and/or decoding the video streams typically includes storing individual video frames in a receive buffer of the client. The video streams may be presented to the user on a display integral to Client 1110 or on a separate device such as a monitor or television. Clients 1110 are optionally configured to support more than one game player. For example, a game console may be configured to support two, three, four or more simultaneous players. Each of these players may receive a separate video stream, or a single video stream may include regions of a frame generated specifically for each player, e.g., generated based on each player's point of view. Clients 1110 are optionally geographically dispersed. The number of clients included in Game System 1100 may vary widely from one or two to thousands, tens of thousands, or more. As used herein, the term "game player" is used to refer to a person that plays a game and the term "game playing device" is used to refer to a device used to play a game. In some embodiments, the game playing device may refer to a plurality of computing devices that cooperate to deliver a game experience to the user. For example, a game console and an HMD may cooperate with the video server system 1120 to deliver a game viewed through the HMD. In one embodiment, the game console receives the video stream from the video server system 1120, and the game console forwards the video stream, or updates to the video stream, to the HMD for rendering.

Clients 1110 are configured to receive video streams via Network 1115. Network 1115 may be any type of communication network including, a telephone network, the Internet, wireless networks, powerline networks, local area networks, wide area networks, private networks, and/or the like. In typical embodiments, the video streams are communicated via standard protocols, such as TCP/IP or UDP/IP. Alternatively, the video streams are communicated via proprietary standards.

A typical example of Clients 1110 is a personal computer comprising a processor, non-volatile memory, a display, decoding logic, network communication capabilities, and input devices. The decoding logic may include hardware, firmware, and/or software stored on a computer readable medium. Systems for decoding (and encoding) video streams are well known in the art and vary depending on the particular encoding scheme used.

Clients 1110 may, but are not required to, further include systems configured for modifying received video. For example, a client may be configured to perform further rendering, to overlay one video image on another video image, to crop a video image, and/or the like. For example, Clients 1110 may be configured to receive various types of video frames, such as I-frames, P-frames and B-frames, and to process these frames into images for display to a user. In some embodiments, a member of Clients 1110 is configured to perform further rendering, shading, conversion to 3-D, optical distortion processing for HMD optics, or like operations on the video stream. A member of Clients 1110 is optionally configured to receive more than one audio or video stream. Input devices of Clients 1110 may include, for example, a one-hand game controller, a two-hand game controller, a gesture recognition system, a gaze recognition system, a voice recognition system, a keyboard, a joystick, a pointing device, a force feedback device, a motion and/or location sensing device, a mouse, a touch screen, a neural interface, a camera, input devices yet to be developed, and/or the like.

The video stream (and optionally audio stream) received by Clients 1110 is generated and provided by Video Server System 1120. As is described further elsewhere herein, this video stream includes video frames (and the audio stream includes audio frames). The video frames are configured (e.g., they include pixel information in an appropriate data structure) to contribute meaningfully to the images displayed to the user. As used herein, the term "video frames" is used to refer to frames including predominantly information that is configured to contribute to, e.g. to effect, the images shown to the user. Most of the teachings herein with regard to "video frames" can also be applied to "audio frames."

Clients 1110 are typically configured to receive inputs from a user. These inputs may include game commands configured to change the state of the video game or otherwise affect game play. The game commands can be received using input devices and/or may be automatically generated by computing instructions executing on Clients 1110. The received game commands are communicated from Clients 1110 via Network 1115 to Video Server System 1120 and/or Game Server 1125. For example, in some embodiments, the game commands are communicated to Game Server 1125 via Video Server System 1120. In some embodiments, separate copies of the game commands are communicated from Clients 1110 to Game Server 1125 and Video Server System 1120. The communication of game commands is optionally dependent on the identity of the command. Game commands are optionally communicated from Client 1110A through a different route or communication channel that that used to provide audio or video streams to Client 1110A.

Game Server 1125 is optionally operated by a different entity than Video Server System 1120. For example, Game Server 1125 may be operated by the publisher of a multiplayer game. In this example, Video Server System 1120 is optionally viewed as a client by Game Server 1125 and optionally configured to appear from the point of view of Game Server 1125 to be a prior art client executing a prior art game engine. Communication between Video Server System 1120 and Game Server 1125 optionally occurs via Network 1115. As such, Game Server 1125 can be a prior art multiplayer game server that sends game state information to multiple clients, one of which is game server system 1120. Video Server System 1120 may be configured to communicate with multiple instances of Game Server 1125 at the same time. For example, Video Server System 1120 can be configured to provide a plurality of different video games to different users. Each of these different video games may be supported by a different Game Server 1125 and/or published by different entities. In some embodiments, several geographically distributed instances of Video Server System 1120 are configured to provide game video to a plurality of different users. Each of these instances of Video Server System 1120 may be in communication with the same instance of Game Server 1125. Communication between Video Server System 1120 and one or more Game Server 1125 optionally occurs via a dedicated communication channel. For example, Video Server System 1120 may be connected to Game Server 1125 via a high bandwidth channel that is dedicated to communication between these two systems.

Video Server System 1120 comprises at least a Video Source 1130, an I/O Device 1145, a Processor 1150, and non-transitory Storage 1155. Video Server System 1120 may include one computing device or be distributed among a plurality of computing devices. These computing devices are optionally connected via a communications system such as a local area network.

Video Source 1130 is configured to provide a video stream, e.g., streaming video or a series of video frames that form a moving picture. In some embodiments, Video Source 1130 includes a video game engine and rendering logic. The video game engine is configured to receive game commands from a player and to maintain a copy of the state of the video game based on the received commands. This game state includes the position of objects in a game environment, as well as typically a point of view. The game state may also include properties, images, colors and/or textures of objects. The game state is typically maintained based on game rules, as well as game commands such as move, turn, attack, set focus to, interact, use, and/or the like. Part of the game engine is optionally disposed within Game Server 1125. Game Server 1125 may maintain a copy of the state of the game based on game commands received from multiple players using geographically disperse clients. In these cases, the game state is provided by Game Server 1125 to Video Source 1130, wherein a copy of the game state is stored and rendering is performed. Game Server 1125 may receive game commands directly from Clients 1110 via Network 1115, and/or may receive game commands via Video Server System 1120.

Video Source 1130 typically includes rendering logic, e.g., hardware, firmware, and/or software stored on a computer readable medium such as Storage 1155. This rendering logic is configured to create video frames of the video stream based on the game state. All or part of the rendering logic is optionally disposed within a graphics processing unit (GPU). Rendering logic typically includes processing stages configured for determining the three-dimensional spatial relationships between objects and/or for applying appropriate textures, etc., based on the game state and viewpoint. The rendering logic produces raw video that is then usually encoded prior to communication to Clients 1110. For example, the raw video may be encoded according to an Adobe Flash® standard, .wav, H.264, H.263, On2, VP6, VC-1, WMA, Huffyuv, Lagarith, MPG-x. Xvid.FFmpeg, x264, VP6-8, realvideo, mp3, or the like. The encoding process produces a video stream that is optionally packaged for delivery to a decoder on a remote device. The video stream is characterized by a frame size and a frame rate. Typical frame sizes include 800×600, 1280×720 (e.g., 720p), 1024×768, although any other frame sizes may be used. The frame rate is the number of video frames per second. A video stream may include different types of video frames. For example, the H.264 standard includes a "P" frame and a "I" frame. I-frames include information to refresh all macro blocks/pixels on a display device, while P-frames include information to refresh a subset thereof. P-frames are typically smaller in data size than are I-frames. As used herein the term "frame size" is meant to refer to a number of pixels within a frame. The term "frame data size" is used to refer to a number of bytes required to store the frame.

In alternative embodiments Video Source 1130 includes a video recording device such as a camera. This camera may be used to generate delayed or live video that can be included in the video stream of a computer game. The resulting video stream, optionally includes both rendered images and images recorded using a still or video camera. Video Source 1130 may also include storage devices configured to store previously recorded video to be included in a video stream. Video Source 1130 may also include motion or positioning sensing devices configured to detect motion or position of an object, e.g., person, and logic configured to determine a game state or produce video-based on the detected motion and/or position.

Video Source 1130 is optionally configured to provide overlays configured to be placed on other video. For example, these overlays may include a command interface, log in instructions, messages to a game player, images of other game players, video feeds of other game players (e.g., webcam video). In embodiments of Client 1110A including a touch screen interface or a gaze detection interface, the overlay may include a virtual keyboard, joystick, touch pad, and/or the like. In one example of an overlay a player's voice is overlaid on an audio stream. Video Source 1130 optionally further includes one or more audio sources.

In embodiments wherein Video Server System 1120 is configured to maintain the game state based on input from more than one player, each player may have a different point of view comprising a position and direction of view. Video Source 1130 is optionally configured to provide a separate video stream for each player based on their point of view. Further, Video Source 1130 may be configured to provide a different frame size, frame data size, and/or encoding to each of Client 1110. Video Source 1130 is optionally configured to provide 3-D video.

I/O Device 1145 is configured for Video Server System 1120 to send and/or receive information such as video, commands, requests for information, a game state, gaze information, device motion, device location, user motion, client identities, player identities, game commands, security information, audio, and/or the like. I/O Device 1145 typically includes communication hardware such as a network card or modem. I/O Device 1145 is configured to communicate with Game Server 1125, Network 1115, and/or Clients 1110.

Processor 1150 is configured to execute logic, e.g. software, included within the various components of Video Server System 1120 discussed herein. For example, Processor 1150 may be programmed with software instructions in order to perform the functions of Video Source 1130, Game Server 1125, and/or a Client Qualifier 1160. Video Server System 1120 optionally includes more than one instance of Processor 1150. Processor 1150 may also be programmed with software instructions in order to execute commands received by Video Server System 1120, or to coordinate the operation of the various elements of Game System 1100 discussed herein. Processor 1150 may include one or more hardware device. Processor 1150 is an electronic processor.

Storage 1155 includes non-transitory analog and/or digital storage devices. For example, Storage 1155 may include an analog storage device configured to store video frames. Storage 1155 may include a computer readable digital storage, e.g. a hard drive, an optical drive, or solid state storage. Storage 1115 is configured (e.g. by way of an appropriate data structure or file system) to store video frames, artificial frames, a video stream including both video frames and artificial frames, audio frame, an audio stream, and/or the like. Storage 1155 is optionally distributed among a plurality of devices. In some embodiments, Storage 1155 is configured to store the software components of Video Source 1130 discussed elsewhere herein. These components may be stored in a format ready to be provisioned when needed.

Video Server System 1120 optionally further comprises Client Qualifier 1160. Client Qualifier 1160 is configured for remotely determining the capabilities of a client, such as Clients 1110A or 1110B. These capabilities can include both the capabilities of Client 1110A itself as well as the capabilities of one or more communication channels between Client 1110A and Video Server System 1120. For example, Client Qualifier 1160 may be configured to test a communication channel through Network 1115.

Client Qualifier 1160 can determine (e.g., discover) the capabilities of Client 1110A manually or automatically. Manual determination includes communicating with a user of Client 1110A and asking the user to provide capabilities. For example, in some embodiments, Client Qualifier 1160 is configured to display images, text, and/or the like within a browser of Client 1110A. In one embodiment, Client 1110A is an HMD that includes a browser. In another embodiment, client 1110A is a game console having a browser, which may be displayed on the HMD. The displayed objects request that the user enter information such as operating system, processor, video decoder type, type of network connection, display resolution, etc. of Client 1110A. The information entered by the user is communicated back to Client Qualifier 1160.

Automatic determination may occur, for example, by execution of an agent on Client 1110A and/or by sending test video to Client 1110A. The agent may comprise computing instructions, such as java script, embedded in a web page or installed as an add-on. The agent is optionally provided by Client Qualifier 1160. In various embodiments, the agent can find out processing power of Client 1110A, decoding and display capabilities of Client 1110A, lag time reliability and bandwidth of communication channels between Client 1110A and Video Server System 1120, a display type of Client 1110A, firewalls present on Client 1110A, hardware of Client 1110A, software executing on Client 1110A, registry entries within Client 1110A, and/or the like.

Client Qualifier 1160 includes hardware, firmware, and/or software stored on a computer readable medium. Client Qualifier 1160 is optionally disposed on a computing device separate from one or more other elements of Video Server System 1120. For example, in some embodiments, Client Qualifier 1160 is configured to determine the characteristics of communication channels between Clients 1110 and more than one instance of Video Server System 1120. In these embodiments the information discovered by Client Qualifier can be used to determine which instance of Video Server System 1120 is best suited for delivery of streaming video to one of Clients 1110.

Embodiments may be practiced with various computer system configurations including hand-held devices, microprocessor systems, microprocessor-based or programmable consumer electronics, minicomputers, mainframe computers and the like. The embodiments can also be practiced in distributed computing environments where tasks are performed by remote processing devices that are linked through a network.

With the above embodiments in mind, it should be understood that the embodiments can employ various computer-implemented operations involving data stored in computer systems. These operations are those requiring physical manipulation of physical quantities. Any of the operations described herein that form part of the embodiments are useful machine operations. The embodiments also relate to a device or an apparatus for performing these operations. The apparatus may be specially constructed for the required purpose, such as a special purpose computer. When defined as a special purpose computer, the computer can also perform other processing, program execution or routines that are not part of the special purpose, while still being capable of operating for the special purpose. Alternatively, the operations may be processed by a general purpose computer selectively activated or configured by one or more computer programs stored in the computer memory, cache, or obtained over a network. When data is obtained over a network the data may be processed by other computers on the network, e.g., a cloud of computing resources.

One or more embodiments can also be fabricated as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing, as long as the processing of the overlay operations are performed in the desired way.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the embodiments are not to be limited to the details given herein, but may be modified within the scope and equivalents of the appended claims.

What is claimed is:

1. A method executed by a processor, comprising:
monitoring physical characteristics of a user while the user is wearing a headmounted display (HMD) and the HMD is presenting a virtual reality with multimedia content, the multimedia content including video for presentation on a display of the HMD and audio, the physical characteristics including motions of the user;
determining if the user is experiencing motion sickness based on the monitoring of the physical characteristics of the user while the virtual reality is being presented, the physical characteristics include eye movement that is not expected based on presentation of the multimedia content, the eye movement is detected using gaze detection from within the HMD, wherein said eye movement is one of the physical characteristics used to determine that the user is experiencing motion sickness; and delivering supplemental sound to the user upon said determining that the user is experiencing motion sickness, wherein the supplemental sound is output via speakers interfaced with ears of the user while wearing the HMD, the sound from the multimedia content is output via the speakers interfaced with the ears along with the supplemental sound, the supplemental sound is delivered at a frequency that is preconfigured to not interfere with a sound fidelity of the sound from the multimedia content, the supplemental sound being defined to decrease the motion sickness experienced by the user.

2. The method as recited in claim 1, wherein the physical characteristics further include one or more of user body motion, or user pupil motion detected by said eye movement, or user head motion, or user balance.

3. The method as recited in claim 1, further including:
lowering a game intensity of a game executing on the HMD to reduce the motion sickness, the game generating the virtual reality for display on the HMD.

4. The method as recited in claim 1, further including:
vibrating the HMD in a vibrating pattern defined to further decrease the motion sickness.

5. The method as recited in claim 1, wherein monitoring physical characteristics of the user further includes:
monitoring motions of the user with sensor data obtained by sensors in the HMD.

6. The method as recited in claim 1, wherein monitoring physical characteristics of the user further includes:
monitoring motions of the user with image data obtained by a camera outside the HMD.

7. The method as recited in claim 1, wherein the supplemental sound is determined based on a profile of the user, the profile of the user including an age of the user.

8. The method as recited in claim 1, further including:
generating microwave stimulation for a vestibular system of the user.

9. The method as recited in claim 1, further including:
initiating an exit process for the user when the motion sickness is beyond a predetermined threshold.

10. The method as recited in claim 1, wherein the supplemental sound includes one or more of acoustic pulses, or a continuous acoustic signal, or an ultrasonic sound.

11. A headmounted display (HMD) comprising:
a display for presenting a virtual reality with multimedia content;
speakers for presenting sound of the multimedia content, the speakers are part of headphones to be worn over ears of a user;
a camera for tracking a gaze of the user when the user is wearing the HMD, the camera is disposed inside the HMD and directed toward an eye of the user when viewing a screen within the HMD; and
a processor, wherein the processor determines if the user is experiencing motion sickness based on the tracking of the gaze of the user, wherein when the user is experiencing motion sickness, the speakers deliver supplemental sound at a frequency that is preconfigured to not interfere with a sound fidelity of the sound of the multimedia content, the supplemental sound defined to decrease the motion sickness experienced by the user, wherein the supplemental sound is output simultaneously with sound from the multimedia content for delivery via the speakers to the user.

12. The HMD as recited in claim 11, wherein the processor determines if the user is experiencing motion sickness by detecting erratic user gaze, or detecting erratic pupil motion from said tracking of the gaze of the user.

13. The HMD as recited in claim 11, wherein the processor further takes input to determine if the user is experiencing motion sickness by additionally processing one or more of detecting the user losing balance, or detecting a lack of response of the user to game challenges.

14. The HMD as recited in claim 11, wherein the virtual reality is generated by a game executing on the HMD.

15. The HMD as recited in claim 11, wherein the processor additionally lowers a game intensity of a game executing on the HMD to reduce the motion sickness, the game generating the virtual reality for display on the HMD.

16. A non-transitory computer-readable storage medium storing a computer program, the computer-readable storage medium comprising:
program instructions for monitoring physical characteristics of a user wearing a headmounted display (HMD) while the user is accessing a virtual reality with multimedia content on the HMD;
program instructions for determining if the user is experiencing motion sickness based on the physical characteristics; and
program instructions for delivering supplemental sound to the user upon said determining that the user is experiencing motion sickness, the supplemental sound defined to decrease the motion sickness experienced by the user, wherein the supplemental sound is output via speakers interfaced with ears of the user while wearing the HMD, the sound from the multimedia content is output via the speakers interfaced with the ears along with the supplemental sound, the supplemental sound is delivered at a frequency that is preconfigured to not interfere with a sound fidelity of the sound from the multimedia content; and
program instructions for additionally lowering an intensity of the multimedia content when the user is determined to be experiencing motion sickness, the lowering of intensity includes slowing down action of movement in the multimedia content or reducing a number of background elements being displayed for the multimedia content.

17. The storage medium as recited in claim 16, wherein the physical characteristics include one or more of user body motion, or user pupil motion, or user gaze, or user head motion, or user balance.

18. The storage medium as recited in claim 16, further including:
program instructions for vibrating the HMD in a vibrating pattern defined to further decrease the motion sickness.

19. The storage medium as recited in claim 16, wherein monitoring physical characteristics of the user further includes:
program instructions for monitoring motions of the user with sensor data obtained by sensors in the HMD.

* * * * *